United States Patent [19]

Hagen et al.

[11] Patent Number: 5,035,736
[45] Date of Patent: Jul. 30, 1991

[54] HERBICIDES WHICH CONTAIN 2-(4-HETARYLOXY)- OR 2-(4-ARYLOXY)-PHENOXYACETIC OR -PROPIONIC ACID DERIVATIVES AND/OR CYCLOHEXENONE DERIVATIVES AS HERBICIDAL ACTIVE INGREDIENTS AND NAPHTHALENE DERIVATIVES AS ANTIDOTES AND FOR CONTROLLING PLANT GROWTH

[75] Inventors: Helmut Hagen, Frankenthal; Juergen Pfister, Speyer; Ulrich Eichenauer, Frankfurt; Bruno Wuerzer, Otterstadt; Wilfried Helbig, Neustadt; Karl-Otto Westphalen, Speyer, all of Fed. Rep. of Germany

[73] Assignee: BASF Aktiengesellschaft, Ludwigshafen, Fed. Rep. of Germany

[21] Appl. No.: 429,763

[22] Filed: Oct. 31, 1989

[30] Foreign Application Priority Data

Nov. 9, 1988 [DE] Fed. Rep. of Germany ....... 3837926

[51] Int. Cl.$^5$ ............................................. A01N 31/04
[52] U.S. Cl. .......................................... 71/98; 71/105; 71/121; 71/127; 71/88; 71/90; 71/91
[58] Field of Search .................. 71/98, 105, 121, 127, 71/88, 90, 91

[56] References Cited

U.S. PATENT DOCUMENTS 2,512,044  6/1950  Swaney et al. ...................... 71/127
3,475,480 10/1969  Habibi .................................. 71/105
4,249,937  2/1981  Iwataki et al. ......................... 71/98

FOREIGN PATENT DOCUMENTS 2080685  2/1982  United Kingdom .

OTHER PUBLICATIONS

Tomioka, Y. et al., "Studies on Aromatic Nitro Compounds, V. a Simple One-Pot Preparation of O-Aminoaroylnitriles from some Aromatic Nitro Compounds", Chem. Pharm. Bull., vol. 33(4), 1360–1366 (1985).
CA 97, 34706c, 1982, CA 97, 34707d, 1982, CA 97, 34708e, 1982, CA 97, 67811m, 1982, CA 97, 2264r, 1982, CA 97, 19038t, 1982, all Abstracts.

Primary Examiner—Glennon H. Hollrah
Assistant Examiner—John Pak
Attorney, Agent, or Firm—Keil & Weinkauf

[57] ABSTRACT

Herbicidal agents containing, as antagonistic agent, at least one naphthalene derivative of the formula I

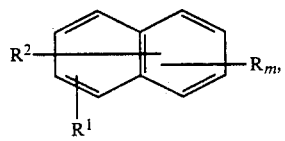

where R, $R^1$, $R^2$, and m are as defined in the specification and at least one herbicidal active ingredient from the group consisting of
(a) 2(4-heteroaryloxy)- or 2-(4-aryloxy)-phenoxyacetic acid derivatives and
(b) cyclohexenone derivatives.

12 Claims, No Drawings

HERBICIDES WHICH CONTAIN 2-(4-HETARYLOXY)- OR 2-(4-ARYLOXY)-PHENOXYACETIC OR -PROPIONIC ACID DERIVATIVES AND/OR CYCLOHEXENONE DERIVATIVES AS HERBICIDAL ACTIVE INGREDIENTS AND NAPHTHALENE DERIVATIVES AS ANTIDOTES AND FOR CONTROLLING PLANT GROWTH

The present invention relates to herbicides which contain 2-(4-hetaryloxy)- or 2-(4-aryloxy)-phenoxyacetic or -propionic acid derivatives and/or cyclohexenone derivatives as herbicidal active ingredients and naphthalene derivatives as antidotes, and methods for selectively controlling undesirable plant growth with these herbicides.

Herbicidal active ingredients from the group consisting of the 2-(4-hetaryloxy)- or 2-(4-aryloxy)phenoxyacetic acid derivatives of the formula II

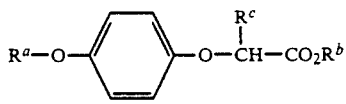

where
$R^a$ is a phenyl ring, a pyridyl ring, a benzoxazyl radical, a benzothiazyl radical or a benzopyrazinyl radical, and these aromatic ring systems may carry one or two of the following radicals: halogen, $C_1$-$C_4$-alkyl, $C_1$-$C_4$-haloalkyl, or nitro,
$R^b$ is hydrogen, $C_1$-$C_4$-alkyl or one equivalent of a plant-tolerated cation and
$R^c$ is hydrogen or methyl, or from the group consisting of the cyclohexenone derivatives of the formula III

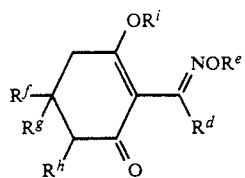

where
$R^d$ is $C_1$-$C_4$-alkyl,
$R^e$ is $C_1$-$C_4$-alkyl, $C_3$- or $C_4$-alkenyl, $C_3$- or $C_4$-alkynyl, $C_3$- or $C_4$-haloalkylene or thenyl which may be substituted by halogen,
$R^f$ is $C_1$-$C_4$-alkyl which may be monosubstituted by $C_1$-$C_4$-alkylthio or $C_1$-$C_4$-alkoxy,
a 5-membered or 6-membered saturated or monounsaturated ring system which, in addition to carbon members, may contain an oxygen or sulfur atom, and the sulfur atom may carry one or two oxygen atoms and this ring may carry up to three of the following radicals: hydroxyl, halogen, $C_1$-$C_4$-alkyl, $C_1$-$C_4$-haloalkyl, $C_1$-$C_4$-alkoxy and/or $C_1$-$C_4$-alkylthio,
a 10-membered saturated or monounsaturated heterocyclic structure which contains two oxygen or sulfur atoms and may be substituted by up to three $C_1$-$C_4$-alkyl groups and/or methoxy groups,
phenyl, pyridyl or isoxazolyl, and this ring may carry up to three of the following groups: $C_1$-$C_4$-alkyl, $C_1$-$C_4$-haloalkyl, $C_1$-$C_4$-alkoxy, $C_1$-$C_4$-alkylthio, $C_3$-$C_6$-alkenyloxy, $C_3$-$C_6$-alkynyloxy, $C_1$-$C_4$-alkoxy-$C_1$-$C_3$-alkyl, $C_1$-$C_4$-dialkoxy-$C_1$-$C_3$-alkyl, formyl, halogen and/or benzoylamino,
$R^g$ is hydrogen or $C_1$-$C_6$-alkyl,
$R^h$ is hydrogen, cyano, halogen or $C_1$-$C_4$-alkoxycarbonyl and
$R^i$ is hydrogen or one equivalent of an environmentally compatible cation, are known from the literature.

2-(4-Hetaryloxy)- or 2-(4-aryloxy)-phenoxyacetic acid derivatives (e.g. DE-A Nos. 22 23 894, 24 33 067, 30 04 770, BE-A Nos. 868 875 and 858 618) are used for controlling undesirable plants from the family of the Gramineae. However, the toleration of these substances by crops varies from commercially acceptable to non-tolerated, depending on the substituents and application rate.

Cyclohexenone derivative herbicides are likewise described in the literature (e.g. EP-A Nos. 228 598, 230 235, 238 021, U.S. Pat. No. 4,432,786 and DE-A No. 24 39 104). They are used predominantly for controlling undesirable grasses in dicotyledon crops and in grasses which do not belong to the family of the Gramineae. Depending on the structure of the substituents and the application rate, compounds from this group can also be used for selectively controlling undesirable grasses in Gramineae crops, such as wheat and rice.

Naphthalene derivatives are described in the literature, both as herbicides and as antidotes of the formula I'

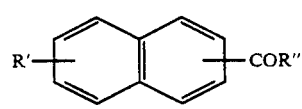

where the substituents have, inter alia, the following meanings: R' is hydrogen, halogen, nitro, $C_1$-$C_5$-alkyl or phenyl and R'' is hydroxyl, alkoxy, alkylthio, amino or substituted amino (HU-A Nos. 21 318, 21 319, 21 320, 21 321, 21 322, 21 323 and BE No. 884 634). These antidotes are recommended for reducing damage caused by herbicides of the following classes: ureas, thiocarbamates, triazines, chloroacetanilide derivatives and uracil derivatives.

It is an object of the present invention to provide compounds which are capable of counteracting the damage caused to crops by herbicides of the (hetaryloxy)- or (aryloxy)-phenoxyacetic acid or cyclohexenone type.

We have found that this object is achieved and that naphthalene derivatives of the formula I

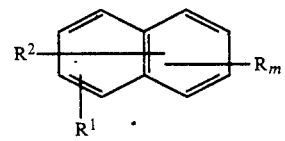

where
R is $C_1$-$C_4$-alkyl, $C_1$-$C_4$-alkylthio, $C_1$-$C_4$-haloalkyl, $C_1$-$C_4$-alkoxy, halogen, hydroxyl, nitro or benzyl,
m is 0, 1, 2 or 3, and the radicals R may be different when m is 2 or 3,
$R^1$ is —CN, —C(NH$_2$)NOH or —C(X)YR$^3$,

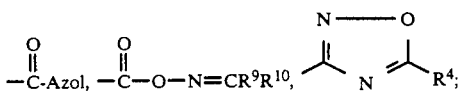

$R^2$ is halogen, $-NR^5R^6$, $-N=CH-R^5$, $-NR^5-SO_2R^7$, $COOR^3$, OH

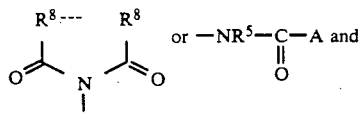 or $-NR^5-\underset{\underset{O}{\|}}{C}-A$ and

X is oxygen or sulfur,
Y is oxygen or $-NR^3$,
$R^3$ is hydrogen,
$C_1-C_6$-alkyl which may carry from one to three of the following substituents: halogen, $C_1-C_4$-alkylamino, di-($C_1-C_4$-alkyl)-amino, $C_1-C_4$-alkoxy or $C_1-C_4$-alkylthio,
phenyl or benzyl which may carry from one to three of the following groups: $C_1-C_4$-alkyl, $C_1-C_4$-alkoxy, $C_1-C_4$-alkylthio, $C_1-C_4$-haloalkyl, cyano, nitro and/or halogen,
$R^4$ is phenyl which may carry one or two of the following groups: halogen, $C_1-C_4$-alkyl, $C_1-C_4$-alkoxy, $C_1-C_4$-alkylthio, $C_1-C_4$-haloalkyl, cyano and/or nitro,
$R^5$ is hydrogen or
$C_1-C_6$-alkyl which may carry from one to three of the following substituents: halogen, $C_1-C_4$-alkylamino, di-($C_1-C_4$-alkyl)-amino, $C_1-C_4$-alkoxy, $C_1-C_4$-alkylthio, phenyl and/or ($C_1-C_4$-alkyl)-oxycarbonyl, or
phenyl which may carry from one to three of the following substituents: halogen, $C_1-C_4$-alkyl, $C_1-C_4$-alkoxy, $C_1-C_4$-alkylthio, $C_1-C_4$-haloalkyl, cyano and/or nitro,
$R^6$ is hydrogen or
$C_1-C_6$-alkyl which may carry from one to three of the following substituents: halogen, $C_1-C_4$-alkylamino, di-($C_1-C_4$-alkyl)-amino, $C_1-C_4$-alkoxy, $C_1-C_4$-alkylthio and/or phenyl,
$R^7$ is $C_1-C_6$-alkyl which may carry from one to three of the following substituents: $C_1-C_4$-alkoxy, $C_1-C_4$-alkylthio, $C_1-C_4$-alkylamino, di-($C_1-C_4$-alkyl)-amino, phenyl and/or from one to five halogen atoms, or
phenyl or 5-membered or 6-membered hetaryl, and these rings may carry from one to three of the following groups: $C_1-C_4$-alkyl, $C_1-C_4$-alkoxy, $C_1-C_4$-alkylthio, $C_1-C_4$-haloalkyl, nitro, cyano and/or halogen,
$R^8$ is $C_1-C_6$-alkyl or $C_2-C_6$-alkenyl, and these groups may carry from one to three of the following substituents: halogen, $C_1-C_4$-alkoxy, $C_1-C_4$-alkylthio and/or phenyl, or phenyl which may carry from one to three of the following substituents: $C_1-C_4$-alkyl, $C_1-C_4$-alkoxy, $C_1-C_4$-alkylthio, $C_1-C_4$-haloalkyl, nitro, cyano and/or halogen, or $R^8$... $R^8$ together form a $C_2-C_4$-alkylene or $C_2-C_4$-alkenylene chain, and these bridges may carry up to three of the following substituents: $C_1-C_4$-alkyl, $C_1-C_4$-alkoxy, $C_1-C_4$-alkylthio, halogen and/or phenyl, or may form a fused benzene ring which may carry from one to four halogen atoms and/or from one to three of the following radicals: $C_1-C_4$-alkyl, $C_1-C_4$-alkoxy, $C_1-C_4$-alkylthio, $C_1-C_4$-haloalkyl, cyano, nitro and/or phenyl,
$R^9$ and $R^{10}$ are each $C_1-C_4$-alkyl or, together with the carbon atom to which they are bonded, are $C_3-C_6$-cycloalkyl, and
A is hydrogen,
$C_1-C_6$-alkyl which may carry from one to three of the following substituents: halogen, $C_1-C_4$-alkoxy, $C_1-C_4$-alkylthio, $C_1-C_4$-alkylamino, di-($C_1-C_4$-alkyl)-amino, phenyl and/or $C_1-C_4$-alkoxycarbonyl,
$C_1-C_4$-alkoxycarbonyl,
$-NR^5R^6-$ or
phenyl which may carry from one to five halogen atoms and/or from one to three of the following substituents: $C_1-C_4$-alkyl, $C_1-C_4$-alkoxy, $C_1-C_4$-haloalkyl, cyano and/or nitro,
are very suitable for protecting crops from the family of the Gramineae and improve the toleration of the herbicides of the (hetaryloxy)- or aryloxyphenoxyacetic acid or cyclohexenone type, especially in crops such as cereals, rice, corn and sorghum. The damage to the crops is reduced or completely prevented. Undesirable grass species are controlled, and whether these herbicides, consisting of herbicidal active ingredient and antidote, are formulated and applied together or separately or, in the case of separate application, the order in which the herbicidal active ingredient and the antidote are applied is unimportant with regard to the action.

The compounds I are prepared by methods conventionally used in the literature.

Derivatives I in which $R^1$ and $R^2$ occupy adjacent ring positions are obtained, for example, by reacting a corresponding nitronaphthyl derivative IV under conditions similar to those described by Y. Tomioka (Chem. Pharm. Bull. 33 (4) (1985), 1360-1366) to give the cyanonaphthylamine Ia ($R^1=CN$, $R^2=NH_2$). This reaction sequence is shown for the synthesis of 2-aminonaphthalene-1-carbonitrile derivatives in the scheme below:

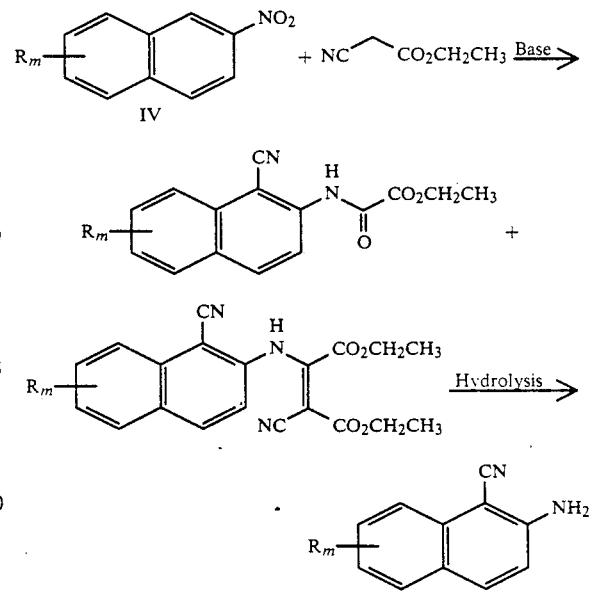

From the derivatives Ia, the corresponding compounds I can be synthesized by the derivatization methods conventionally used in the literature (derivatives of the cyano group: Methoden der organ. Chem. (Houben- Weyl) Volume E5, page 263 et seq., page 710 et seq., page 790 et seq., page 941 et seq., page 1242 et seq., and page 1313; Volume X/4 (1968), page 209 et seq.; derivatives of the amino group: Methoden der organ. Chem. (Houben-Weyl) Volume XI (2), page 3 et seq. and Volume V (2), page 846).

The synthesis of the naphthalene derivatives I in which $R^1$ and $R^2$ do not occupy adjacent ring positions can be carried out in a variety of ways and is described in the literature. The literature references are listed together with the corresponding compounds in Tables 1 and 2 after the Synthesis Examples.

Regarding the biological activity, preferred naphthalene derivatives are those in which R is alkyl, such as methyl, ethyl, propyl, 1-methylethyl, butyl, 1-methylpropyl, 2-methylpropyl or 1,1-dimethylethyl, in particular methyl or ethyl, haloalkyl, such as fluoromethyl, difluoromethyl, trifluoromethyl, 2,2-difluoroethyl, 2,2,2-trifluoroethyl or 1,2,2-trifluoroethyl, in particular trifluoromethyl or 2,2,2-trifluoroethyl, alkoxy such as methoxy, ethoxy, propoxy, isopropoxy or tert-butoxy, in particular methoxy or ethoxy, alkylthio, such as methylthio, ethylthio, isopropylthio or tert-butylthio, in particular methylthio, halogen, such as fluorine, chlorine, bromine or iodine, in particular fluorine, chlorine or bromine, hydroxyl, nitro or benzyl, m is 0, 1, 2 or 3, and the radicals R may be different when m is 2 or 3, and $R^1$ is cyano, a carboxamine oxime, a carboxylic acid, a thiocarboxylic acid, a carboxamide, a thiocarboxamide, oxadiazole, an iminoester group, where $R^9$ and $R^{10}$ are each methyl, ethyl, propyl, butyl, cyclopentyl or cyclohexyl, or is a radical —C(O)-azole, where azole is 1-imidazolyl, 1-pyrazolyl or, in particular, 1-triazolyl.

If $R^1$ is an acid function or an amide function, this radical may additionally be substituted by one of the abovementioned alkyl groups, by a phenyl radical or by a benzyl radical.

The following are particularly preferred:
cyano,
carboxamide and thiocarboxamide radicals which are unsubstituted or substituted by methyl, ethyl, phenyl and/or benzyl, and
3-oxadiazolyl radcials which are substituted in the 5-position by a phenyl ring, where this phenyl ring may in turn carry up to three substituents. Suitable substituents here are the halogen atoms, alkyl, alkoxy, alkylthio, haloalkyl and/or cyano or nitro groups already mentioned under R.

$R^2$ may be halogen, as stated under R, fluorine, chlorine and bromine being preferred.

$R^2$ may furthermore be a carboxylic acid group, a hydroxyl group, an amino group or a derivative of a hydroxyl group or of an amino group. The following are particularly preferred:
dialkylamino, such as dimethylamino and diethylamino,
diacylamino, such as diacetylamino, maleimino, dichloromaleimino, methylmaleimino, phthalimino, tetrabromophthalimino and 3,4,5,6-tetrahydrophthalimino,
acylamino, such as acetylamino, glutarylamino, benzoylamino and ethyloxaloylamino,
sulfonylamino, such as phenylsulfonylamino and N-(phenylsulfonyl)-N-(1-carboxyl)-methylamino, and
imino, such as benzalimino.

Suitable derivatives of hydroxyl groups are salts, such as alkali metal salts or esters with inorganic or organic acids, such as alkylsulfonic acids, phosphoric acids or carboxylic acids.

Very particularly preferred compounds I are those in which $R^1$ and $R^2$ occupy adjacent ring positions.

Specific examples of herbicidal (hetaryloxy)- and aryloxyphenoxyacetic acid derivatives of the formula II whose toleration by crops can be improved by naphthalene derivatives of the formula I are listed in Table A below:

TABLE A $$R^a-O-\langle\text{phenyl}\rangle-O-\underset{R^c}{\underset{|}{CH}}-CO_2R^b \qquad II$$

| No. | $R^a$ | $R^b$ | $R^c$ | References |
|---|---|---|---|---|
| II.1 | 2,4-dichlorophenyl | CH₃ | CH₃ | DE-A 22 23 894 |
| II.2 | 5-trifluoromethyl-2-pyridyl | n-C₄H₉ | CH₃ | BE-A 868 875 |
| II.3 | 2-(N-acetyl)-4-chlorophenyl | C₂H₅ | CH₃ | BE-A 858 618 |
| II.4 | 3-chloro-5-trifluoromethyl-2-pyridyl | CH₃ | CH₃ | BE-A 868 875 |
| II.5 | 3-chloro-quinoxalin-2-yl | C₂H₅ | CH₃ | DE-A 30 04 770 |

Specific examples of cyclohexenones of the formula III whose toleration by crops can be improved by naphthalene derivatives of the formula I are listed in Table B below.

TABLE B

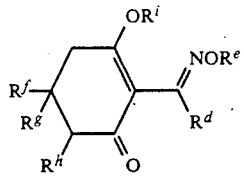

III

| No. | $R^d$ | $R^e$ | $R^f$ | $R^g$ | $R^h$ | $R^i$ | References |
|---|---|---|---|---|---|---|---|
| III.1 | $C_3H_7$ | $CH_2CH=CH_2$ | $CH_3$ | $CH_3$ | $CO_2CH_3$ | Na | DE-A 2 439 104 |
| III.2 | $C_3H_7$ | $CH_2CH_3$ | $CH_2CH(CH_3)SCH_2CH_3$ | H | H | H | DE-A 2 822 304 |
| III.3 | $C_2H_5$ | $CH_2CH=CHCl$ | $CH_2CH(CH_3)SCH_2CH_3$ | H | H | H | US-A 4 440 566 |
| III.4 | $C_3H_7$ | $CH_2CH=CHCl$ | $CH_2CH(CH_3)SCH_2CH_3$ | H | H | H | US-A 4 440 566 |
| III.5 | $C_3H_7$ | $C_2H_5$ | ![tetrahydrothiopyranyl] | H | H | H | EP-A 71 707 |
| III.6 | $C_2H_5$ | $C_2H_5$ | ![tetrahydrothiopyranyl] | H | H | H | EP-A 71 707 |
| III.7 | $CH_3$ | $CH_2CH=CHCH_3$ | ![tetrahydrothiopyranyl] | H | H | H | EP-A 71 707 |
| III.8 | $C_3H_7$ | $C_2H_5$ | ![tetrahydropyranyl] | H | H | H | EP-A 71 707 |
| III.9 | $C_2H_5$ | $CH_2CH=CHCl$ | ![tetrahydropyranyl] | H | H | H | EP-A 142 741 |
| III.10 | $C_3H_7$ | $C_2H_5$ | ![pyridyl] | H | H | H | EP-A 66 195 |
| III.11 | $C_2H_5$ | $C_2H_5$ | ![4-methylphenyl] | H | H | H | DE-A 24 39 104 |
| III.12 | $C_2H_5$ | $CH_2CH=CHCH_3$ | ![4-ethylphenyl] | H | H | H | DE-A 38 08 072 |
| III.13 | $C_2H_5$ | $C_2H_5$ | ![2,4,6-trimethylphenyl] | H | H | H | EP-A 880 301 |
| III.14 | $C_3H_7$ | $CH_2CH=CHCl$ | ![4-methylcyclohexyl] | H | H | H | EP-A 88 299 |

TABLE B-continued $$\text{III}$$

Structure: cyclohexanone with OR$^i$ at position 3, =NOR$^e$ substituent on C=R$^d$ at position 2, R$^f$ and R$^g$ at position 5, R$^h$ at position 6.

| No. | R$^d$ | R$^e$ | R$^f$ | R$^g$ | R$^h$ | R$^i$ | References |
|---|---|---|---|---|---|---|---|
| III.15 | C$_3$H$_7$ | CH$_2$CH=CHCH$_3$ | 4-methylcyclohexyl | H | H | H | EP-A 88 299 |
| III.16 | C$_2$H$_5$ | CH$_2$CH=CHCH$_3$ | 3-isopropyl-5-methylisoxazol-4-yl | H | H | H | EP-A 238 021 |
| III.17 | C$_3$H$_7$ | CH$_2$CH=CHCH$_3$ | 3-isopropyl-5-methylisoxazol-4-yl | H | H | H | EP-A 238 021 |
| III.18 | C$_2$H$_5$ | CH$_2$CH=CHCl | 4-(propargyloxy)phenyl | H | H | H | EP-A 137 174 |
| III.19 | C$_3$H$_7$ | C$_2$H$_5$ | 4-(ethoxymethyl)phenyl | H | H | H | EP-A 2 137 200 |
| III.20 | C$_3$H$_7$ | C$_2$H$_5$ | 3,4-dibromotetrahydropyran-3-yl | H | H | H | EP-A 230 235 |
| III.21 | C$_3$H$_7$ | CH$_2$CH=CHCl | 3,4-dibromotetrahydropyran-3-yl | H | H | H | EP-A 230 235 |
| III.22 | C$_2$H$_5$ | C$_2$H$_5$ | 3,4-dihydroxycyclohexyl | H | H | H | EP-A 278 598 |
| III.23 | C$_3$H$_7$ | CH$_2$CH=CHCl | 2,6,6-trimethyl-6,6-dimethylcyclohex-1-enyl | H | H | H | EP-A 46 860 |
| III.24 | C$_3$H$_7$ | C$_2$H$_5$ | cyclohexyl | H | H | H | JP-A 540 191 945 |

TABLE B-continued

Structure III:

$$\text{cyclohexenone with } OR^i, =NOR^e, R^d, R^f, R^g, R^h \text{ substituents}$$

| No. | $R^d$ | $R^e$ | $R^f$ | $R^g$ | $R^h$ | $R^i$ | References |
|---|---|---|---|---|---|---|---|
| III.25 | $C_3H_7$ | $C_2H_5$ | cyclohexenyl | H | H | H | EP-A 46 860 |
| III.26 | $CH_3$ | $CH_2CH=CHCl$ | 4-methylcyclohexyl | H | H | H | EP-A 88 299 |
| III.27 | $C_3H_7$ | $C_2H_5$ | 4-(trifluoromethyl)phenyl | H | H | K | EP-A 137 174 |
| III.28 | $C_2H_5$ | $CH_2CH=CHCl$ | 2,6,6-trimethylcyclohexenyl | H | H | H | EP-A 46 860 |

Synthesis Examples

EXAMPLE 1

2-Benzoylaminonaphthalene-1-carbonitrile

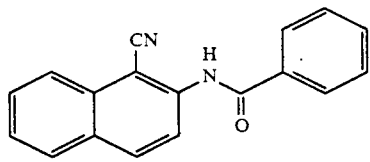

3.0 g (17.8 millimoles) of 2-aminonaphthalene-1-carbonitrile (Chem. Pharm. Bull 33 (4) (1985), 1360–1366) were stirred with 2.5 g (18.1 millimoles) of benzoyl chloride and 4 ml of triethylamine in 100 ml of toluene for 15 hours at 80° C. After the end of the reaction, the product was filtered off and dried. 1.5 g (31% of theory) of the title compound of melting point 205° C. (active ingredient example 1008) were obtained in this manner.

EXAMPLE 2

1-(N-phthalimido)-naphthalene-2-carbonitrile

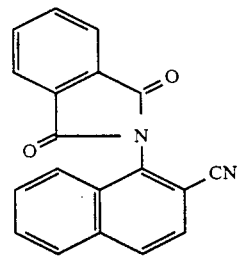

3.0 g (17.9 millimoles) of 1-aminonaphthalene-2-carbonitrile (Chem. Pharm. Bull 33 (4) (1985), 1360–1366) and 2.7 g (17.9 millimoles) of phthalic anhydride in 40 ml of concentrated acetic acid were heated at the boil for 15 hours. After the end of the reaction, the reaction mixture was stirred into 200 ml of water, and the precipitate was isolated and dried. 3.5 g (66% of theory) of the title compound of melting point 196° C. (active ingredient example 2010) were obtained in this manner.

EXAMPLE 3

5-(3-Chlorophenyl)-3-(1'-aminonaphth-2'-yl)-oxadiazole

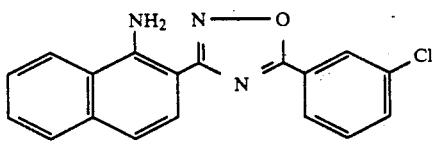

(a) 1-Aminonaphthalene-2-carboxamide oxime

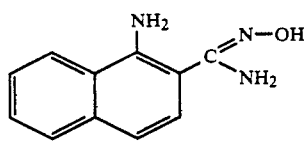

33.6 g (0.20 mole) of 1-aminonaphthalene-2-carbonitrile (Chem. Pharm. Bull. 33 (1985), 1360-1366), 18.8 g (0.27 mole) of hydroxylammonium chloride and 22.7 g (0.27 mole) of sodium bicarbonate in 300 ml of 3:2 ethanol/water were refluxed for 15 hours. The mixture was cooled and the product was then filtered off under suction and washed with n-propanol. 30.0 g (75%) of the title compound of melting point 178°–180° C. (active ingredient example 2031) were obtained.

(b) 6.0 g (30 millimoles) of the compound obtained under (a), 6.9 ml (50 millimoles) of methyl 3-chlorobenzoate and 3.2 g (60 millimoles) of sodium methylate in 70 ml of methanol were heated at the boil for 15 hours. After the end of the reaction, the mixture was stirred into 500 ml of water, and the precipitated product was filtered off and dried. 5.4 g (56% of theory) of the title compound of melting point 160° C. (active ingredient example 2069) were obtained in this manner.

EXAMPLE 4

2-Chloronaphthalene-1-carbonitrile

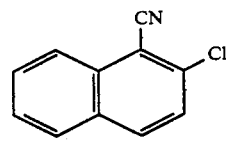

33.6 g (0.2 mole) of 2-aminonaphthalene-1-carbonitrile (cf. Example 1) in 250 ml of absolute acetonitrile were added at 65° C. to a suspension of 32.3 g (0.24 mole) of copper(II) chloride (anhydrous) and 30.9 g (0.3 mole) of tert-butylnitrile in 800 ml of absolute acetonitrile. After the end of gas evolution, 2,000 ml of 20% strength hydrochloric acid were added to the cooled reaction mixture, and the precipitate was isolated, washed and dried. 31.7 g (70% of theory) of the title compound of melting point 82°–83° C. (active ingredient example 1001) were obtained in this manner.

TABLE 1

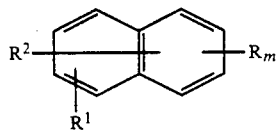

| No. | $R^1$ | $R^2$ | $R_m$ | mp [°C.] | Literature |
|---|---|---|---|---|---|
| 1.001 | 1-CN | 2-Cl | | 98–99 | Chem. Ber. 83, 171 (1950) |
| 1.002 | 1-CN | 2-Br | | 85–86 | |
| 1.003 | 1-CN | 2-NH$_2$ | | 122 | Chem. Pharm. Bull 33, 1360 (1985) |
| 1.004 | 1-CN | 2-NH$_2$ | 6-OCH$_3$ | | J. Org. Chem. 33, 1719 (1968) |
| 1.005 | 1-CN | 2-NHCOCH$_3$ | | 164 | Monatsh. Chem. 89, 358 (1958) |
| 1.006 | 1-CN | 2-N(COCH$_3$)$_2$ | | 111–113 | as 1.005 |
| 1.007 | 1-CN | 2-NHCO(CH$_2$)$_2$CO$_2$H | | 204 | |
| 1.008 | 1-CN | 2-NHCOPh | | 205 | |
| 1.009 | 1-CN | 2-NHCONHPh | | 270 | |
| 1.010 | 1-CN | 2-NHCOCO$_2$CH$_2$CH$_3$ | | 162 | as 1.003 |
| 1.011 | 1-CN | 2-N=CHPh | | 112–113 | as 1.005 |
| 1.012 | 1-CN | 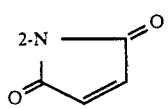 | | 148 | |
| 1.013 | 1-CN | 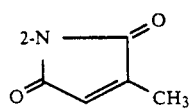 | | 96 | |
| 1.014 | 1-CN | 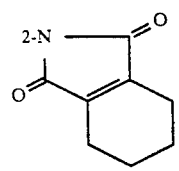 | | 83 | |

TABLE 1-continued

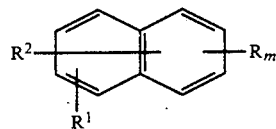

| No. | R¹ | R² | $R_m$ | mp [°C.] | Literature |
|---|---|---|---|---|---|
| 1.015 | 1-CN | 2-N(phthalimide) | | 139 | |
| 1.016 | 1-CN | 2-N(tetrabromophthalimide) | | >260 | |
| 1.017 | 1-CN | 3-NH$_2$ | | 116–118 | Bull. Soc. Chim. Fr. 234 (1954) |
| 1.018 | 1-CN | 3-NHCOCH$_3$ | | 260 | as 1.017 |
| 1.019 | 1-CN | 4-Cl | | 110 | Chem. Ber. 28, 1840 |
| 1.020 | 1-CN | 4-NH$_2$ | | 174 | Ber. Dts. Chem. Ges. 28, 1842 |
| 1.021 | 1-CN | 4-NH$_2$ | 2-CH$_3$ | 188 | J. Am. Chem. Soc. 78, 4774 (1956) |
| 1.022 | 1-CN | 4-NH$_2$ | 3-NO$_2$ | 239.5 | CA 3353 (1956) |
| 1.023 | 1-CN | 4-NHCOCH$_3$ | | 189.5 | as 1.022 |
| 1.024 | 1-CN | 4-NHCOCH$_3$ | 3-NO$_2$ | 270.5 | as 1.022 |
| 1.025 | 1-CN | 4-NHSO$_2$Ph | 3-CH$_3$ | 183–184 | J. Am. Chem. Soc. 79, 170 (1957) |
| 1.026 | 1-CN | 4-NHSO$_2$Ph (N-CH$_2$CO$_2$H) | 3-CH$_3$ | 195.5–196.5 | as 1.025 |
| 1.027 | 1-CN | 5-Cl | | 148 | J. Chem. Soc. P.T.I. 2779 (1979) |
| 1.028 | 1-CN | 5-Br | | 147 | Chem. Ber. 9, 1516 |
| 1.029 | 1-CN | 5-NH$_2$ | | 139–140 | (a) J. Chem. Soc. 678 (1954)979) (b) J. Am. Chem. Soc. 63, 828 (1941) |
| 1.030 | 1-CN | 5-NHCOCH$_3$ | | | |
| 1.031 | 1-CN | 5-NHCOPh | | 211–212 | Helv. Chim. Acta 8, 8419 (1979) |
| 1.032 | 1-CN | 6-Cl | | | |
| 1.033 | 1-CN | 6-Br | | | |
| 1.034 | 1-CN | 6-NH$_2$ | | | |
| 1.035 | 1-CN | 7-Cl | | | |
| 1.036 | 1-CN | 7-Br | | | |
| 1.037 | 1-CN | 7-NH$_2$ | | | |
| 1.038 | 1-CN | 8-Cl | | 145 | as 1.027 |
| 1.039 | 1-CN | 8-Br | | | |
| 1.040 | 1-CN | 8-NH$_2$ | | 88 | Bull. Soc. Chim. Fr. 1561 (1972) |
| 1.041 | 1-CONH$_2$ | 2-Cl | | 144 | |
| 1.042 | 1-CONH$_2$ | 2-Br | | | |
| 1.043 | 1-CONH$_2$ | 2-NH$_2$ | | | |
| 1.044 | 1-CONH$_2$ | 5-Br | | 240–241 | as 1.028 |
| 1.045 | 1-CONH$_2$ | 5-NH$_2$ | | | |
| 1.046 | 1-CONH$_2$ | 8-Cl | | | |
| 1.047 | 1-CONH$_2$ | 8-NH$_2$ | | 233 | as 1.040 |
| 1.048 | 1-CSNH$_2$ | 2-Cl | | | |
| 1.049 | 1-CSNH$_2$ | 2-Br | | | |
| 1.050 | 1-CSNH$_2$ | 2-NH$_2$ | | | J. Prakt. Chem. 319, 65 (1977) |
| 1.051 | 1-CO$_2$H | 2-Cl | | | |
| 1.052 | 1-CO$_2$H | 2-NH$_2$ | | | |
| 1.053 | 1-CO$_2$H | 3-Cl | | 223 | J. Chem. Soc. 1426 (1958) |
| 1.054 | 1-CO$_2$H | 3-NH$_2$ | | 179 | Chem. Ber. 90, 2876 (1957) |
| 1.055 | 1-CO$_2$H | 4-Br | | 221 | as 1.053 |
| 1.056 | 1-CO$_2$H | 4-NH$_2$ | | 177 | Z. Obsc. Chim. 231, 1028 (1953) |
| 1.057 | 1-CO$_2$H | 4-N(CH$_3$)$_2$ | | 161 | J. Chem. Soc. 1310 (1959) |
| 1.058 | 1-CO$_2$H | 5-Cl | | | |
| 1.059 | 1-CO$_2$H | 5-Cl | 8-NO$_2$ | 224–225 | J. Prakt. Chem. 38, 155 |
| 1.060 | 1-CO$_2$H | 5-Br | | 242 | as 1.059 |
| 1.061 | 1-CO$_2$H | 5-Br | 8-NO$_2$ | 260 | as 1.059 |
| 1.062 | 1-CO$_2$H | 5-NH$_2$ | | 212–213 | J. Chem. Soc. 991 (1950) |
| 1.063 | 1-CO$_2$H | 7-Cl | | | |
| 1.064 | 1-CO$_2$H | 7-NH$_2$ | | 228–229 | J. Org. Chem. 13, 164 (1948) |
| 1.065 | 1-CO$_2$H | 7-NHCOCH$_3$ | | 237–238 | as 1.064 |

TABLE 1-continued

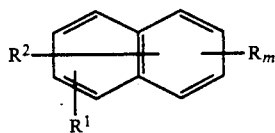

| No. | R¹ | R² | R_m | mp [°C.] | Literature |
|---|---|---|---|---|---|
| 1.066 | 1-CO₂H | 8-Cl | | | |
| 1.067 | 1-CO₂H | 8-Br | | | |
| 1.068 | 1-CO₂H | 8-NH₂ | 5-Br | 250 | Helv. Chim. Acta 15, 1366 (1932) |
| 1.069 | 1-CO₂CH₂CH₃ | 3-Cl | | | |
| 1.070 | 1-CO₂CH₂CH₃ | 3-Br | | 28 | as 1.053 |
| 1.071 | 1-CO₂CH₃ | 4-F | | bp₂₀ = 123 | J. Chem. Soc. 310 (1959) |
| 1.072 | 1-CO₂CH₂CH₃ | 4-F | | | |
| 1.073 | 1-CO₂CH₂CH₃ | 4-NH₂ | | | |
| 1.074 | 1-CO₂CH₂CH₃ | 4-N(CH₃)₂ | | bp₁ = 152 | as 1.057 |
| 1.075 | 1-CO₂(CH₂)₂NHC₃H₇ | 4-NH₂ | | 208 | Z. Obsc. Chim. 22, 328 (1952) |
| 1.076 | 1-CO₂H | 2-CO₂H | 6-CH₃ | | |
| 1.077 | 1-CO₂H | 2-OH | 6-CH₃ | | |
| 1.078 | 1-CO₂H | 5-OH | 2-Cl, 6-CH₃ | | |
| 1.079 | 1-C(=O)-N(N=CH-CH=N) (triazole) | H | 2,7-Cl₂ | | |
| 1.080 | 1-C(=O)-ON=C(CH₃)₂ | H | 2,7-Cl₂ | | |
| 1.081 | 1-C(=O)-ON=cyclohexyl | H | 2,7-Cl₂ | 155–158 | |
| 1.082 | 1-CN | 2-NHC(=O)-(2,4-Cl₂-C₆H₃) | | 134–136 | |
| 1.083 | 1-CO₂H | 4-Cl | | | DE-A 20 28 255 |
| 1.084 | 1-CO₂H | 2-Cl | 6-Cl | 150–152 | |
| 1.085 | 1-CO₂CH₃ | 2-Cl | 6-Cl | | |
| 1.086 | 1-CO₂C₄H₉ | 2-Cl | 6-Cl | oil | |
| 1.087 | 1-CO₂C₆H₁₃ | 2-Cl | 6-Cl | 51–53 | |
| 1.088 | 1-CO₂H | 2-Cl | 6-CH₃ | 188–190 | |
| 1.089 | 1-CO₂H | 2-Cl | 5-NO₂, 6-Cl | 179 | |
| 1.090 | 1-C(=O)-N(CH(CH₃)C₂H₅)₂ | 4-Cl | | oil | DE-A 20 28 555 |
| 1.091 | 1-C(=O)-N(i-C₃H₇)₂ | 4-Cl | | | DE-A 20 28 555 |
| 1.092 | 1-C(=O)-N(CH₃)₂ | 2-Cl | 6-Cl | 139–142 | |
| 1.093 | 1-C(=O)-N(CH(CH₃)C₂H₅)₂ | 2-Cl | 6-Cl | | |
| 1.094 | 1-CN | 2-OH | | | |

TABLE 2

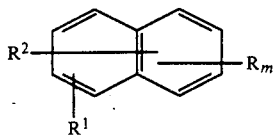

| No. | R¹ | R² | $R_m$ | mp [°C.] | Literature |
|---|---|---|---|---|---|
| 2.001 | 2-CN | 1-Cl | | 101–102 | |
| 2.002 | 2-CN | 1-Br | | 85–86 | |
| 2.003 | 2-CN | 1-Br | 6-Br | 178 | as 1.053 |
| 2.004 | 2-CN | 1-NH₂ | | 109 | as 1.040, 1.003 |
| 2.005 | 2-CN | 1-NH₂ | 3-CH₂Ph | | |
| 2.006 | 2-CN | 1-NHCOCH₃ | | 219.5–220.5 | Rec. Trav. Chim. Pays-Bas 76, 401 (1957) |
| 2.007 | 2-CN | (maleimide-N) | | >260 | |
| 2.008 | 2-CN | (dichloromaleimide-N) | | 222 | |
| 2.009 | 2-CN | (succinimide-N) | | 186 | |
| 2.010 | 2-CN | (phthalimide-N) | | 196 | |
| 2.011 | 2-CN | 3-NH₂ | | 163–164 | Bull. Soc. Chim. Fr. 743 (1954) |
| 2.012 | 2-CN | 3-NH₂ | 4-Br | 154–155 | as 1.050 |
| 2.013 | 2-CN | 3-Cl | | | |
| 2.014 | 2-CN | 3-Br | | | |
| 2.015 | 2-CN | 4-Cl | | | |
| 2.016 | 2-CN | 4-Br | | | |
| 2.017 | 2-CN | 4-NH₂ | | 125–126 | as 1.029(b) |
| 2.018 | 2-CN | 5-Cl | | 142 | as 1.027 |
| | | | | 144 | J. Prakt. Chem. 43, 412 |
| 2.019 | 2-CN | 5-Cl | 8-Cl | 140 | as 1.053 |
| 2.020 | 2-CN | 5-NH₂ | | 143–144 | as 1.029(b) |
| 2.021 | 2-CN | 6-Cl | | | |
| 2.022 | 2-CN | 6-NH₂ | | 199 | as 1.029(b) |
| 2.023 | 2-CN | 7-Cl | | | |
| 2.024 | 2-CN | 7-Br | | | |
| 2.025 | 2-CN | 7-NH₂ | | 197 | as 1.029(a) |
| 2.026 | 2-CN | 8-Cl | | 112–113 | as 1.027 |
| 2.027 | 2-CN | 8-Br | | | |
| 2.028 | 2-CN | 8-NH₂ | | 133 | DRP 92 995 |
| 2.029 | 2-C(NH₂)=NOH | 1-Cl | | | |
| 2.030 | 2-C(NH₂)=NOH | 1-Br | | | |
| 2.031 | 2-C(NH₂)=NOH | 1-NH₂ | | 164–166 | |
| 2.032 | 2-CONH₂ | 1-Cl | | 144 | |
| 2.033 | 2-CONH₂ | 1-Br | | | |
| 2.034 | 2-CONH₂ | 1-NH₂ | | 107–108 | (a) as 1.050 |
| | | | | 191–192 | (b) Chem. Ber. 98, 2556 (1965) |
| 2.035 | 2-CONH₂ | 3-Cl | | | |
| 2.036 | 2-CONH₂ | 3-NH₂ | | 234–236 | (a) as 1.040 |
| | | | | | (b) Liebigs Am. Chem. 516, 248 (1935) |
| 2.037 | 2-CONH₂ | 3-NH₂ | 4-Br | | as 1.050 |
| 2.038 | 2-CONH₂ | 3-NHCOCH₃ | | 240 | as 2.036 |
| 2.039 | 2-CONHCH₂Ph | 3-NH₂ | | 210 | DRP 514 596 (1928) |
| 2.040 | 2-CON(Ph)CH₃ | 3-NH₂ | | 165 | as 2.039 |
| 2.041 | 2-CONH₂ | 5-Cl | | 186–187 | as 2.018 |
| 2.042 | 2-CONH₂ | 5-Cl | 8-Cl | 218 | as 1.053 |
| 2.043 | 2-CONH₂ | 5-NH₂ | | | |
| 2.044 | 2-CSNH₂ | 1-Cl | | | |
| 2.045 | 2-CSNH₂ | 1-NH₂ | | 193–194 | as 1.050 |

TABLE 2-continued

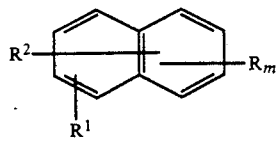

| No. | R¹ | R² | R_m | mp [°C.] | Literature |
|---|---|---|---|---|---|
| 2.046 | 2-CSNH$_2$ | 3-Cl | | | |
| 2.047 | 2-CSNH$_2$ | 3-NH$_2$ | | 182–187 (decomp.) | as 1.050 |
| 2.048 | 2-CO$_2$H | 1-F | | | |
| 2.049 | 2-CO$_2$H | 1-Br | | 160–161 | |
| 2.050 | 2-CO$_2$H | 1-NH$_2$ | | 203–205 | as 1.056 |
| 2.051 | 2-CO$_2$H | 3-F | 4-Br | 235–236 | Chem. Ber. 92, 1999 (1952) |
| 2.052 | 2-CO$_2$H | 3-Cl | | | |
| 2.053 | 2-CO$_2$H | 3-NH$_2$ | | | |
| 2.054 | 2-CO$_2$H | 5-Cl | | 263 | as 2.018 |
| 2.055 | 2-CO$_2$H | 5-J | | 254 | J. Chem. Soc. 2794 (1958) |
| 2.056 | 2-CO$_2$H | 5-NH$_2$ | | | |
| 2.057 | 2-CO$_2$H | 8-Cl | | | |
| 2.058 | 2-CO$_2$H | 8-Br | | | |
| 2.059 | 2-CO$_2$H | 8-NH$_2$ | | 215–216 | J. Am. Chem. Soc. 74, 3652 (1952) |
| 2.060 | 2-CO$_2$CH$_2$CH$_3$ | 1-Cl | | | |
| 2.061 | 2-CO$_2$CH$_2$CH$_3$ | 1-NH$_2$ | | | |
| 2.062 | 2-CO$_2$CH$_2$CH$_3$ | 3-Cl | | | |
| 2.063 | 2-CO$_2$CH$_2$CH$_3$ | 3-NH$_2$ | | 117–118 | as 2.039 |
| 2.064 | 2-CO$_2$CH$_2$CH$_3$ | 5-Cl | | 45 | as 2.018 |
| 2.065 | 2-CO$_2$CH$_2$CH$_3$ | 5-NH$_2$ | | | |
| 2.066 | 2-CO$_2$CH$_2$CH$_3$ | 8-Cl | | 29 | as 2.018 |
| 2.067 | 2-CO$_2$CH$_2$CH$_3$ | 8-NH$_2$ | | | |
| 2.068 | (oxadiazole-phenyl) | 1-NH$_2$ | | 132–134 | |
| 2.069 | (oxadiazole-3-chlorophenyl) | 1-NH$_2$ | | 160 | |
| 2.070 | (oxadiazole-3-chlorophenyl) | 1-Cl | | 160 | |
| 2.071 | (oxadiazole-4-methylphenyl) | 1-Cl | | | |
| 2.072 | (oxadiazole-4-methylphenyl) | 1-NH$_2$ | | 141–142 | |
| 2.073 | 2-CO$_2$C$_6$H$_5$ | 1-Br | | oil | |
| 2.074 | 2-C(=O)-NH-n-C$_4$H$_9$ | 1-Br | | 118–119 | |
| 2.075 | 2-C(=O)-N(C$_2$H$_5$)$_2$ | 1-Br | | oil | |
| 2.076 | 2-CO$_2$H | 6-Cl | | 281–282 | |
| 2.077 | 2-CO$_2$CH$_3$ | 3-NH$_2$ | | 84–86 | |

TABLE 2-continued

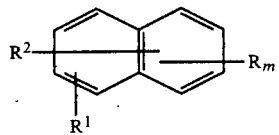

| No. | $R^1$ | $R^2$ | $R_m$ | mp [°C.] | Literature |
|---|---|---|---|---|---|
| 2.078 | 2-CO$_2$CH$_3$ | | 6-Br | | |
| 2.079 | 2-CNHC$_6$H$_5$<br>‖<br>O | | 1-Br | 136–145 | |

Examples demonstrating biological action

The influence of various representatives of the herbicidal agents, or combinations consisting of herbicide and safener according to the invention, on the growth of unwanted and crop plants compared with that of the herbicidal active ingredient alone is demonstrated by the following biological experiments carried out in the greenhouse.

The vessels employed were plastic flowerpots having a volume of 300 cm$^3$ and filled with a sandy loam containing about 3.0% humus. The seeds of the test plants were sown shallow, and separately, according to species. The soil was then moistened. After the agents had been applied, transparent plastic covers were then placed on the vessels until the plants had uniformly germinated and the plants had taken root.

For the postemergence treatment, the plants were grown, depending on growth form, to a height of 3 to 20 cm before being treated. The herbicidal agents were suspended or emulsified in water as vehicle and sprayed through finely distributing nozzles.

Compound II.3 serves as an example of a 2-(4-heteroaryloxy)-phenoxy acid derivative of the formula II:

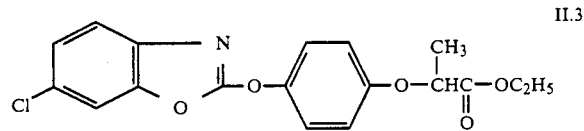

II.3

The cyclohexenone derivatives III listed in the biological examples are:

[Structure III: cyclohexenone with OH, =NOR$^2$, R$^1$, R$^3$ substituents]

| No. | $R^3$ | $R^1$ | $R^2$ |
|---|---|---|---|
| III.2 | H$_5$C$_2$SCHCH$_2$—<br>\|<br>CH$_3$ | C$_3$H$_7$ | C$_2$H$_5$ |
| III.12 | H$_5$C$_2$—[phenyl]— | C$_2$H$_5$ | —CH$_2$—CH=CH—CH$_3$ |
| III.16 | H$_3$C\,CH—[isoxazole with CH$_3$]<br>H$_3$C/ | C$_2$H$_5$ | —CH$_2$CH=CHCH$_3$ |
| III.13 | [2,4,5-trimethylphenyl] | C$_2$H$_5$ | C$_2$H$_5$ |

-continued $$\text{III}$$

Structure III: cyclohexenone with OH, R³ substituent, and =NOR² / R¹ group, with =O.

| No. | R³ | R¹ | R² |
|---|---|---|---|
| III.5 | (tetrahydrothiopyranyl group) | C₃H₇ | C₂H₅ |

The herbicidal active ingredients and antidotes may be applied together or separately to the leaves and shoots of the crop plants and unwanted plants. Preferably, the antidote is applied together with the herbicidal active ingredient. If the components are applied separately, the antidote is applied first to the field and then the herbicidal active ingredient. The herbicidal active ingredient and antidote may be formulated together or separately as spray agents in the form of suspensions, emulsions or solutions.

Treatment of the crop plant seed with the antidote prior to sowing is also feasible. The herbicidal active ingredient is then applied to the field on its own in conventional manner.

For herbicidal (heteroaryloxy)-phenoxy acid derivatives of the formula II, the amount of antidotally active compound varies, depending on the crop. The ratios may vary over a wide range, and are also dependent on the structure of the (heteroaryloxy)phenoxy acid derivatives II and on the crop involved. Suitable ratios of herbicidal active ingredient to antidote are from 1:40 to 1:0.01, and preferably from 1:4 to 1:0.1, parts by weight.

For the same cyclohexenone derivative III, the amount of antidote varies, depending on the crop. The ratios in which a cyclohexenone derivative III and a naphthalene derivative I are used may vary over a wide range, and are dependent on the structure of the cyclohexenone derivative, the naphthalene derivative and the crop involved. Suitable ratios of herbicidal active ingredient to safener are from 1:40 to 1:0.01, and preferably from 1:4 to 1:0.25, parts by weight.

The novel herbicidal agents may contain, in addition to the naphthalene derivative I as safener and the herbicide from the group of the (heteroaryloxy)phenoxyacetic acids II or cyclohexenones III, other herbicidal or growth-regulating active ingredients having a different chemical structure without the safening effect being impaired.

The agents according to the invention, or—when applied separately—the herbicidal active ingredients and the safener, are applied for instance in the form of directly sprayable solutions, powders, suspensions (including high-percentage aqueous, oily or others), dispersions, emulsions, oil dispersions, pastes, dusts, broadcasting agents or granules by spraying, atomizing, dusting, broadcasting or pouring. The forms of application depend entirely on the purpose for which the active ingredients are to be used.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, alkali metal and alkaline earth metal salts of dibutylnaphthalenesulfonic acid, lauryl ether sulfate, fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient and safener. The amounts of herbicidal active ingredient applied range from 0.2 to 5 kg/ha.

The herbicidal active ingredient III.2 is added (on its own and together with the safener) as a commercially formulated product (184 g/l of emulsion concentrate (EC)) to the spray liquor together with the amounts of solvent system given in the tables.

In the case of the other herbicidal active ingredients, no solvent system was added if the herbicide was not combined with a safener.

They were formulated as follows:

III.12, III.16 and III.13 as 100 g/l of EC; II.3 as 120 g/l of EC; and III.5 as 200 g/l of EC.

All safeners were formulated in a mixture consisting of 80% solvent and 20% surfactant, together with 10 wt % of active ingredient.

The vessels were set up in the greenhouse, heat-loving species at from 18° to 35° C. and species from more moderate climates at from 10° to 25° C.

The experiment was run for from 3 to 5 weeks. During this period, the plants were tended and their reactions to the various treatments assessed. Damage by the chemical agents was assessed on a scale from 0 to 100% compared with the untreated control plants, 0 denoting no damage and 100 denoting complete destruction of the plants.

| List of test plants: | |
|---|---|
| Botanical name | Common name |
| Avena fatua | wild oats |
| Hordeum vulgare | barley |
| Lolium multiflorum | annual raygrass |
| Oryza sativa | rice |
| Setaria faberii | giant foxtail |
| Setaria italica | foxtail millet |
| Setaria viridis | green foxtail |
| Triticum aestivum | wheat |
| Zea mays | Indian corn |

The tables below document the antidotal action, compounds nos. 1.001, 1.002, 1.003, 1.041, 1.076, 1.077, 1.078, 1.079 and 2.004 improving the tolerance by crop plants of the cyclohexenone derivatives III.2, III.12, III.16, III.13 and III.5 and of the (heteroaryloxy)-phenoxy acid derivative II.3.

TABLE 3

Improved tolerance of the herbicide sethoxydim III.2 by wheat by adding safeners; postemergence application in the greenhouse

| | Appln. rate kg/ha | Test plants and damage in % | |
|---|---|---|---|
| Safener No. | III.2 Safener | Crop plant wheat* | Unwanted plant Lolium multifl. |
| — | 0.015 — | 50 | 100 |
| | 0.03 — | 65 | 100 |
| 1.003 | 0.015 + 0.06 | 10 | 100 |
| | 0.03 + 0.125 | 25 | 100 |
| 1.002 | 0.015 + 0.06 | 10 | 100 |
| | 0.03 + 0.125 | 25 | 100 |
| 1.041 | 0.015 + 0.06 | 10 | 100 |
| | 0.03 + 0.125 | 10 | 100 |

*"Okapi" variety

TABLE 4

| | Appl. rate kg/ha | Test plants and damage in % | |
|---|---|---|---|
| Safener No. | III.2 Safener | Crop plant wheat** | Unwanted plant Setaria viridis |
| — | 0.0125 — | 40 | 95 |
| | 0.025 — | 90 | 98 |
| 1.003 | 0.0125 + 0.025 | 0 | 90 |
| | 0.025 + 0.05 | 0 | 100 |

**"Okapi" variety

TABLE 5

Improvement in the tolerance of the herbicide sethoxydim III.2 by the crop plant Indian corn by adding safening compounds; postemergence application in the greenhouse

| | Appl. rate kg/ha | Test plants and damage in % | |
|---|---|---|---|
| Safener No. | III.2 Safener | Crop plant Indian corn** | Unwanted plant Lolium multifl. |
| — | 0.015 — | 65 | 100 |
| | 0.03 — | 80 | 100 |
| 2.004 | 0.015 + 0.06 | 0 | 98 |
| | 0.03 + 0.125 | 20 | 100 |
| 1.001 | 0.015 + 0.06 | 30 | 100 |
| | 0.03 + 0.125 | 20 | 100 |
| 1.041 | 0.015 + 0.06 | 0 | 90 |
| | 0.03 + 0.125 | 20 | 90 |
| 1.077 | 0.015 + 0.06 | 0 | 100 |
| | 0.03 + 0.125 | 0 | 100 |
| 1.078 | 0.015 + 0.06 | 0 | 100 |
| | 0.03 + 0.125 | 20 | 100 |
| 1.076 | 0.015 + 0.06 | 0 | 95 |
| | 0.03 + 0.125 | 20 | 100 |

**"Inrakorn" variety

TABLE 6

Improvement in the tolerance of sethoxydim III.2 by rice by adding safener no. 1.003; postemergence treatment in the greenhouse

| | Appl. rate kg/ha | Test plants and damage in % | |
|---|---|---|---|
| Safener No. | III.2 Safener | Crop plant rice** | Unwanted plant Setaria italica |
| 1.003 | 0.015 — | 60 | 98 |
| | 0.015 + 0.125 | 15 | 98 |

**"Bahia" variety

TABLE 7

Improvement in the tolerance of various herbicides by wheat by combining them with safener no. 1.003; postemergence treatment in the greenhouse.

| | Appl. rate kg/ha | Test plants and damage in % | |
|---|---|---|---|
| Herbicidal act. ingr. | III Safener | Crop plant wheat** | Unwanted plant Avena fatua |
| III.12 | 0.125 — | 40 | 100 |
| | 0.25 — | 50 | 100 |
| III.12 | 0.25 + 0.5 | 0 | 95 |
| III.16 | 0.125 — | 20 | 100 |
| | 0.25 — | 50 | 100 |
| III.16 | 0.125 + 0.5 | 0 | 100 |
| | 0.25 + 0.5 | 0 | 100 |
| III.13 | 0.06 — | 20 | 100 |
| | 0.125 — | 50 | 100 |
| III.13 | 0.06 + 0.5 | 0 | 98 |
| | 0.125 + 0.5 | 0 | 95 |

**"Okapi" variety

TABLE 8

Improvement in the tolerance of the herbicide cycloxydim III.5 by barley by adding safener no. 1.003; postemergence treatment in the greenhouse

| Appl. rate kg/ha III.5 Safener | Crop plant barley*** | Unwanted plants Avena fatua | Setaria fab. |
|---|---|---|---|
| 0.015 — | 30 | 100 | 98 |
| 0.03 — | 98 | 100 | 100 |
| 0.015 + 0.5 | 10 | 100 | 98 |
| 0.03 + 0.5 | 20 | 100 | 100 |

***"Igri" variety

TABLE 9

Improvement in the tolerance of fenoxaprop ethyl II.3 by cereals by adding safener no. 1.003; postemergence application in the greenhouse

| Appl. rate kg/ha II.3 Safener | Crop plants barley*** | wheat** | Unwanted plant Setaria fab. |
|---|---|---|---|
| 0.03 — | 30 | 40 | 100 |
| 0.06 — | 60 | 50 | 100 |
| 0.03 + 0.5 | 10 | 0 | 100 |
| 0.06 + 0.5 | 20 | 0 | 100 |

**"Okapi" variety
***"Igri" variety

TABLE 10

Improvement in the tolerance of sethoxydim III.2 by wheat by pre-treating the plants with safener no. 1.003 postemergence in the greenhouse 24 hours prior to treatment with III.2

| Herbicide No. | Appl. rate kg/ha III Safener | Crop plant wheat** | Unwanted plant Lolium multiflorum |
|---|---|---|---|
| III.2 | 0.03 — | 30 | 100 |
|  | 0.03 + 0.125 | 0 | 100 |
|  | 0.03 + 0.5 | 0 | 100 |

**"Jubilar" variety

TABLE 11

Improvement in the tolerance of III.22 by wheat by adding safener no. 1.094 postemergence in the greenhouse

| Herbicide No. | Appl. rate kg/ha III Safener | Crop plant wheat** | Unwanted plant Lolium multiflorum |
|---|---|---|---|
| III.22 | 0.06 — | 18 | 100 |
|  | 0.125 — | 62 | 100 |
|  | 0.06 + 0.25 | 0 | 100 |
|  | 0.06 + 0.125 | 0 | 100 |
|  | 0.125 + 0.5 | 12 | 100 |
|  | 0.125 + 0.125 | 18 | 100 |

TABLE 12

Improvement in the tolerance of III.2 by wheat by adding safener no. 1.094 postemergence in the greenhouse

| Appl. rate kg/ha III.2 Safener | Crop plant wheat** | Unwanted plant Alopecurus myosuroides |
|---|---|---|
| 0.03 — | 30 | 100 |
| 0.06 — | 62 | 100 |
| 0.03  0.03 | 5 | 100 |
| 0.03  0.06 | 0 | 100 |
| 0.03 + 0.125 | 0 | 100 |
| 0.06 + 0.06 | 18 | 98 |
| 0.06 + 0.25 | 5 | 100 |

**"Okapi", "Kanzler" varieties

We claim:

1. Herbicidal composition containing, as antagonistic agent, at least one naphthalene derivative of the formula I $$R^2 \text{—naphthalene—} R_{m'}, R^1$$

where
R is $C_1$–$C_4$-alkyl, $C_1$–$C_4$-alkylthio, $C_1$–$C_4$-haloalkyl, $C_1$–$C_4$-alkoxy, halogen, hydroxyl, nitro or benzyl,
m is 0, 1, 2 or 3, and the radical R may be different when m is 2 or 3,
$R^1$ is —CN, C(X)Y$R^3$,
$R^2$ is halogen; —N$R^5R^6$; —N=CH—$R^5$; or OH
$R^5$ is hydrogen or
$C_1$–$C_6$-alkyl which may carry from one to three of the following substituents: halogen, $C_1$–$C_4$-alkylamino, di-($C_1$–$C_4$-alkyl)amino, $C_1$–$C_4$-alkoxy, $C_1$–$C_4$-alkylthio, phenyl or
phenyl which may carry from one to three of the following substituents: halogen, $C_1$–$C_4$-alkyl, $C_1$–$C_4$-alkoxy, $C_1$–$C_4$-alkylthio, $C_1$–$C_4$-haloalkyl, cyano and/or nitro;
$R^6$ is hydrogen or
$C_1$–$C_6$-alkyl which may carry from one to three of the following substituents: halogen, $C_1$–$C_4$-alkylamino, di-($C_1$–$C_4$-alkyl)amino, $C_1$–$C_4$-alkoxy, $C_1$–$C_4$-alkylthio and/or phenyl;
and at least one herbicidal active ingredient from the group consisting of the cyclohexenone derivatives of the formula III $$\text{III}$$

where
$R^d$ is $C_1$–$C_4$-alkyl,
$R^e$ is $C_1$–$C_4$-alkyl, $C_3$–$C_4$-alkenyl, $C_3$–$C_4$-alkynyl, $C_3$- or $C_4$-haloalkylene or
thenyl which may be substituted by halogen,
$R^f$ is $C_1$–$C_4$-alkyl which may be monosubstituted by $C_1$–$C_4$-alkylthio or $C_1$–$C_4$-alkoxy,
a 5-membered or 6-membered saturated or monounsaturated ring system which, in addition to carbon members, may contain an oxygen or sulfur atom, and the sulfur atom may carry one or two oxygen atoms and this ring may carry up to three of the following radicals: hydroxy, halogen, $C_1$–$C_4$-alkyl, $C_1$–$C_4$-haloalkyl, $C_1$–$C_4$-alkoxy and/or $C_1$–$C_4$-alkylthio;
a 10-membered saturated or monounsaturated heterocyclic structure which contains two oxygen or sulfur atoms and may be substituted by up to three $C_1$–$C_4$-alkyl groups and/or methoxy groups,
phenyl, pyridyl or isoxazolyl, and this ring may carry up to three of the following groups: $C_1$–$C_4$-alkyl, $C_1$–$C_4$haloalkyl, $C_1$–$C_4$-alkoxy, $C_1$–$C_4$-alkylthio, $C_3$–$C_6$-alkenyloxy, $C_3$–$C_6$-alkynyloxy, $C_1$–$C_4$- alkoxy-$C_1$-$C_3$-alkyl, $C_1$-$C_4$-dialkoxy-$C_1$-$C_3$-alkyl, formyl, halogen and/or benzoylamino $R^g$ is hydrogen, $R^h$ is hydrogen, cyano, halogen or $C_1$-$C_4$-alkoxycarbonyl and $R^i$ is hydrogen or one equivalent of an environmentally compatible cation.

2. A herbicidal composition as set forth in claim 1, where the weight ratio of herbicide of the formula II to naphthalene derivative, applied separately or together, is from 1:4 to 1:0.01 parts.

3. A herbicidal composition as set forth in claim 1, where the weight ratio of herbicide of the formula III to naphthalene derivative, applied separately or together, is from 1:4 to 1:0.01 parts.

4. A herbicidal composition as set forth in claim 1, wherein, in formula I, "m" is 0, "$R^1$" is 1-CN, and "$R^2$" is 2-OH.

5. A herbicidal composition as set forth in claim 1, wherein, in formula I, "m" is 0, "$R^1$" is 1-CN, and "$R^2$" is 2-$NH_2$.

6. A herbicidal composition as set forth in claim 1, wherein in the naphthalene derivative of the formula I, $R^1$ is 1-CN, $R^2$ is 2-Br and m is 0 and wherein in the cyclohexenone derivative of the formula III, $R^d$ is n-butyl, $R^e$ is ethyl, $R^f$ is $CH_2CH(CH_3) SCH_2CH_3$ and $R^g$, $R^h$ and $R^i$ are each hydrogen.

7. A process for the selective control of unwanted plant growth, wherein a naphthalene derivative of the formula I as set forth in claim 1 and a cyclohexenone derivative of the formula III as set forth in claim 1 are applied simultaneously or one after the other in any order either before, during or after sowing of the crop plants, or before or during emergence of the crop plants.

8. A process for preventing damage to crop plants by herbicidal cyclohexenone derivatives of the formula III as set forth in claim 1, wherein the seed of the crop plants is treated with an antagonistically effective amount of a naphthalene derivative of the formula I as set forth in claim 1.

9. A process for the selective control of unwanted plant growth, wherein the leaves of the crop plants and unwanted plants are treated, either simultaneously or one after the other, with a naphthalene derivative of the formula I as set forth in claim 1 and with a cyclohexenone derivative of the formula III.

10. A process as set forth in claim 7, wherein the crop plants are barley, wheat, Indian corn, sorghum and rice.

11. A process as set forth in claim 8, wherein the crop plants are barley, wheat, Indian corn, sorghum and rice.

12. A process as set forth in claim 9, wherein the crop plants are barley, wheat, Indian corn, sorghum and rice.

* * * * *